United States Patent [19]

Eckenhoff et al.

[11] 4,300,558

[45] Nov. 17, 1981

[54] SELF-DRIVEN FLUID DISPENSER

[75] Inventors: James B. Eckenhoff, Los Altos; Felix A. Landrau, Milpitas, both of Calif.

[73] Assignee: ALZA Corporation, Palo Alto, Calif.

[21] Appl. No.: 170,079

[22] Filed: Jul. 18, 1980

[51] Int. Cl.³ ............................................. A61M 7/00
[52] U.S. Cl. .................................... 128/260; 106/169
[58] Field of Search .................. 128/260; 424/32-35; 106/169

[56] References Cited

U.S. PATENT DOCUMENTS

| | | | |
|---|---|---|---|
| 3,987,790 | 10/1976 | Eckenhoff et al. | 128/260 |
| 3,995,631 | 12/1976 | Higuchi et al. | 128/260 |
| 4,034,756 | 7/1977 | Higuchi et al. | 128/260 |
| 4,077,407 | 3/1978 | Theeuwes et al. | 128/260 |

*Primary Examiner*—C. Fred Rosenbaum

*Attorney, Agent, or Firm*—Paul L. Sabatine; Edward L. Mandell

[57] ABSTRACT

An improvement in self-driven miniature fluid dispensers is disclosed. The basic components of the dispensers are: an outer rigid semipermeable cellulose membrane that acts as a housing, an inner collapsible bag housed within the membrane that is adapted to contain the fluid, a water-imbibing composition interposed between the outer membrane and the inner bag, and a port that extends from the interior of the bag to the exterior of the dispenser through which the fluid may be charged to and discharged from the dispenser. The improvement lies in using a blend of cellulose acetate butyrate and polymethylmethacrylate to make the outer membrane, thereby forming a membrane of reduced water permeability.

2 Claims, 2 Drawing Figures

SELF-DRIVEN FLUID DISPENSER

DESCRIPTION

1. Technical Field

This invention relates to an improvement in self-driven miniature fluid dispensers that operate by imbibing water from the environment in which they are used.

2. Background Art

The invention is an improvement in fluid dispensers of the type described in commonly owned U.S. Pat. Nos. 3,987,790, 3,995,631 and 4,034,756. Those patents describe a miniature pump whose basic components are: an outer rigid semipermeable housing, an inner elastomeric bag that is adapted to contain the fluid to be dispensed, an osmotically effective composition interposed between the outer housing and the inner bag, and a fluid filling/discharge port that extends from the interior of the bag to the exterior of the dispenser. Other water imbibing compositions, such as water swellable compositions, may be used in place of the osmotically effective solute component if desired. In operation the bag is filled with fluid and the pump is placed in an aqueous environment. Water is imbibed from the environment by the water imbibing composition through the outer semipermeable membrane into the space between the membrane and the bag. Since the membrane is rigid and the bag is collapsible, the bag is squeezed inwardly in response to the influx of water, thereby displacing or pumping the fluid out of the bag via the port. The permeability of the membrane to water controls the rate at which water is imbibed from the environment and thus also directly affects the rate at which the fluid is pumped from the dispenser. The permeability, in turn, is a function of the composition and thickness of the membrane. The time period over which fluid is dispensed depends on the volume of fluid in the bag and the rate at which it is pumped therefrom. Embodiments of such miniature pumps are currently marketed for use in research animals to administer drugs or other substances to the animals in a continuous, constant manner.

The above cited patents suggest using cellulose ester, such as cellulose acetate and cellulose acetate butyrate, for making the outer membrane of the pump. In this regard, cellulose esters may be spray coated onto an inner bag-water imbibing composition subassembly to form membranes of practical thickness that have the requisite physical properties and good resistance to radiation degradation.

U.S. Pat. No. 4,077,407 concerns dispensers that also operate by imbibing water through an outer semipermeable cellulose ester membrane. That patent teaches that various materials may be blended with the cellulose ester that forms the membrane to increase the water permeability thereof.

DISCLOSURE OF INVENTION

The present invention concerns means to reduce the water permeability of the outer cellulosic membrane of the dispensers of the type described in U.S. Pat. Nos. 3,987,790, 3,995,631 and 4,034,756 without affecting adversely its desirable properties. The means involved altering the membrane composition rather than the membrane thickness. The purpose of the reduction is to achieve a corresponding reduction in the fluid dispensing rate and thus prolong the lifetime of the dispenser.

Specifically the invention is an improvement in fluid dispensers that comprise an outer rigid semipermeable membrane that acts as a housing, an inner collapsible bag housed within the membrane that is adapted to contain the fluid, a water-imbibing composition interposed between the outer membrane and the inner bag, and a port that extends from the interior of the bag to the exterior of the dispenser through which the fluid may be charged into the bag and discharged from the bag. The improvement lies in making the outer membrane from a blend consisting essentially of a major proportion by weight of cellulose acetate butyrate and a minor proportion by weight of polymethylmethacrylate.

DESCRIPTION OF EMBODIMENT SHOWN IN DRAWINGS

Figure 1:
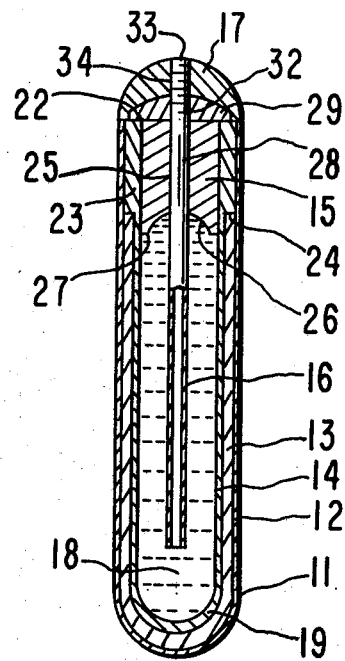
FIG. 1 is an enlarged cross-sectional view of an embodiment of the invention.

FIG. 1 illustrates the preferred embodiment of a fluid dispenser, generally designated 11, to which the present improvement is directed. The basic components of dispenser 11 are: an outer shape-retaining semipermeable membrane 12, an intermediate thermoformed sleeve 13 that includes an osmotically effective solute, an inner collapsible bag 14, a plug 15, a flow moderator 16, and a flow moderator cap 17. This dispenser is the subject matter of commonly owned copending application U.S. Ser. No. 36815 filed May 7, 1979 and now abandoned. The present invention is directed only to the composition of membrane 12. For the sake of completeness, however, the structure and composition of dispenser 11 are described below.

Bag 14 is adapted to contain a fluid composition, such as an active agent composition 18 in fluid form. The term "active agent" as used herein means any compound or mixture of compounds that can be dispensed to produce a predetermined beneficial and useful result. Active agents include pesticides, germicides, biocides, algicides, rodenticides, fungicides, insecticides, antioxidants, plant growth promoters, plant growth inhibitors, preserving agents, surfactants, disinfectants, sterilization agents, catalysts, chemical reactants, fermentation agents, cosmetics, foods, nutrients, food supplements, drugs, vitamins, sex sterilants, fertility inhibitors, fertility promoters, air purifiers, microorganism attenuators, and other compositions that benefit the environment, surroundings, and habitat, including animals and humans. In the preferred embodiment the active agent is a drug that produces a local or systemic physiologic or pharmacologic response when administered to animals or humans.

In order to be a suitable container for the fluid, bag 14 should be substantially impermeable to the fluid composition and be compatible with the composition. By "compatible" it is meant that the bag should not be corroded, solubilized, or otherwise affected deleteriously by the composition. Additionally, when the composition is a drug, the composition should not be significantly contaminated by the bag, such as by the extraction of leachables from the material forming the bag. Bag 14 may be made from elastomeric compositions that may be formed into thin sheets. The elastomeric properties of the elastomeric composition and the thickness of the bag wall should be such as to cause the bag to readily collapse inwardly when a force is applied to the bag exterior. Such elastomeric compositions are disclosed in commonly owned U.S. Pat. No. 3,760,964 at column 5, line 40 to column 7, line 37 and in commonly owned U.S. Pat. No. 3,995,631 at column 8, lines 14-32, which disclosures are incorporated herein by reference.

Bag 14 is elongated and generally cylindrical and is closed at its end 19 and open at its opposite end 22. Its wall is thickened outwardly at 23 to form a shoulder 24. The portion of the exterior of bag 14 below shoulder 24 is encapsulated by sleeve 13 whose wall is approximately as thick as shoulder 24 is wide.

Sleeve 13 is made from a thermoformable osmotically effective solute composition. The components of the composition are an osmotically effective solute and a water soluble, thermoplastic polymer vehicle. The purpose of the solute is to imbibe water from the environment across membrane 12 into the space between the exterior of bag 14 and the inner surface of membrane 12, that is, the space occupied by sleeve 13. Sleeve 13 is thus sealed between membrane 12 and bag 14. The osmotic pressure of the solute when in solution should be significantly greater than the osmotic pressure of the liquid of the environment. In dispensers that are to be ingested by or placed within an animal, the osmotic pressure of the solute solution must exceed the osmotic pressure of body fluids (about 750 kPa). Osmotically effective solutes that may be used in sleeve 13 are disclosed in U.S. Pat. No. 3,760,984 at column 7, line 38 to column 8, line 2 and in U.S. Pat. No. 3,995,631 at page 11, line 65 to column 12, line 3 and column 14, lines 20-28, which disclosures are incorporated herein by reference. Sodium chloride is an especially effective osmotic solute in that the osmotic pressure of sodium chloride is sufficiently high to remove the dependence of pumping rate on the osmotic pressure of the surrounding environment.

The polymer vehicle serves to make the osmotically effective composition thermoformable. Depending upon its osmotic pressure in solution it may also contribute to the osmotic effectiveness of the composition. The vehicle functions as a matrix in which the osmotically effective solute is dispersed and renders the composition flowable upon application of heat and pressure. A preferred vehicle is a mixture of about 40% to about 70% by weight poly(ethylene oxide) having a molecular weight in the range of about 100,000 to about 4,000,000 and about 30% to about 60% by weight poly(ethylene glycol) having a molecular weight in the range of about 1,000 and about 30,000.

In addition to the solute and vehicle the osmotically effective solute composition may contain minor amounts of other materials such as fillers, pigments, lubricants, and other conventional additives that facilitate thermoforming.

As an alternative to sleeve 13, a coating of an osmotically effective solute composition may be applied to the exterior of bag 14. The use of such coatings is disclosed in U.S. Pat. Nos. 3,760,984 and 3,995,631.

Sleeve 13 is encapsulated by outer membrane 12. Membrane 12 also covers the exterior of the portion of bag 14 above shoulder 24 and forms a fluid tight seal therewith. Membrane 12 is impermeable to the components of sleeve 13 and it is shape-retaining, that is, it is sufficiently rigid to be substantially undeformed by the hydrostatic pressure that is generated in the space between it and sleeve 13 by the imbibed water. The composition of membrane 12 is the crux of the present invention. It is composed in major proportion of cellulose acetate butyrate (CAB) and in minor proportion of polymethylmethacrylate (PMMA). Preferably the CAB constitutes from 60% to 90% by weight of the membrane and the PMMA constitutes from 10% to 40% by weight of the membrane. CAB and PMMA are well known, commercially available polymers. Their physical and chemical characteristics are described in the *Handbook of Common Polymers*, Scott et al., CRC Press, 1971. A membrane of given thickness and area made with such CAB-PMMA blends has significantly reduced water permeability relative to a like membrane made from pure cellulose ester or blends of cellulose esters. Thus, in a dispenser 11 of given surface area and dispensing rate, membrane 12 may be made significantly thinner by using the CAB-PMMA blend than would be possible if only cellulose ester was used. The reduction of membrane thickness simplifies the manufacture of the dispenser and minimizes the contribution of membrane 12 to the dimensions of the dispenser. Also, satisfactory mechanical properties (tensile strength, impact resistance and modulus) and chemical and physical stability are not sacrificed by using the CAB-PMMA blend in place of only cellulose ester.

Plug 15 fits into the open end 22 of bag 14. Plug 15 is generally cylindrical and is approximately as long as the thickened portion of bag 14 above shoulder 24. The exterior of plug 15 forms a fluid tight seal with the portion of the interior surface of bag 14 with which it is in contact. Plug 15 has an axial, central bore 25 extending completely through it. Bore 25 provides access to the interior of bag 14 for filling bag 14 with active agent composition 18. Bore 25 is also adapted to receive flow moderator 16. Plug 15 has a hemispherically shaped recess 26 in its inner (bottom) end 27. Plug 15 may be made from the same materials as are used to make flexible bag 14; however, the dimensions of plug 15 should be such that it is substantially inflexible.

Flow modulator 16 provides the passageway from the interior of bag 14 to the exterior of dispenser 11 by which composition 18 is discharged from dispenser 11. Flow moderator 16 comprises a conduit, in the form of a rigid cylindrical tube 28, and a dome-shaped head 29. Tube 28 and head 29 may be made from suitable plastics or metals. Head 29 has an axial, threaded bore 32 that receives threaded end 33 of tube 28. As shown in FIG. 1 end 33 extends outwardly from the spherical surface of head 29 to provide a site for attaching an external catheter tube (not shown) in the event dispenser 11 is to be used to administer composition 18 to remote location. The outer diameter of tube 28 is approximately the same as the diameter of bore 25 such that tube 28 may be inserted through bore 25 into bag 14 with tube 28 fitting snugly within bore 25 so as to form an essentially fluid tight seal with plug 15. The length of tube 28 is such that it extends into bag 14 to at least about 50% of the elongated dimension of the interior of bag 14, i.e., the distance from the inner side of end 19 to end 27 of plug 15. Preferably tube 28 extends into bag 14 over substantially the entire, but not all of (say 85% to 95%), of said elongated dimension. The inner diameter of tube 28 is correlated to the length of tube 28 such that substantial diffusional flow of composition 18 through tube 28 will not occur. Tube 28 is, in effect, a capillary that provides resistance to the flow of composition 18, thereby reducing or eliminating bulk loss of composition 18, from the outlet port of dispenser 11. Head 29 has a diameter slightly less than the outer diameter of plug 15. The flat side of head 29 fits against the top of plug 15.

Dispenser 11 may be filled with fluid 18 via bore 25 of plug 15. For instance, the needle of a fluid-loaded syringe may be inserted through bore 25 and the syringe's contents discharged into bag 14. To insure that a predetermined fluid pumping rate is achieved, it is desirable to completely fill bag 14 with fluid 18. After the bag is filled, tube 28 of flow moderator 16 is inserted through bore 25 to the position shown in FIG. 1. As described above, tube 28 functions as a capillary and inhibits loss of fluid 18 from the dispenser even though it is subjected to substantial movement or tipped upside down.

Dispenser 11 operates in the following manner. Once placed in an aqueous environment, such as within a body cavity or within body tissue, water from the environment is imbibed by the solute of sleeve 13 through membrane 12. The imbibed water causes the volume of the space between the inner surface of membrane 12 and the exterior of bag 14 (the space initially occupied by sleeve 13) to increase. And since membrane 12 is shape-retaining, the imbibed water generates hydraulic pressure on the exterior of bag 14 causing bag 14 to be squeezed inwardly. This squeezing forces fluid 18 through tube 28 and out of the dispenser.

As indicated, fluid 18 may be an active agent composition. In such instances the dispenser 11 will, of course, discharge active agent directly. Alternatively, fluid 18 may be inert and the dispenser may be used simply as a displacement pump. In this alternative the dispenser will, of course, have to be suitably interconnected by well known means to a reservoir of the fluid (active agent) to be discharged, such that the inert fluid displaces the fluid from the reservoir in a predetermined regimen to the desired administration site. Such alternatives are particularly attractive in instances in which the fluid to be discharged is incompatible with bag 14.

Flow modulator cap 17 may be used to cover protruding end 33 of tube 29 when dispenser 11 is used without an external catheter tube connection. Cap 17 is cresent-shaped and has an axial threaded bore 34 that receives end 33 of tube 29. The curvature of its concave underside 35 matches the convexity of the top surface of head 29 so that the former fits tightly against the latter. The outer diameter of cap 17 is the same as the outer diameter of membrane 12. Thus the hemispherical exterior of cap 17 provides a smooth blunt surface that aligns with the exterior surface of membrane 12.

The components of dispenser 11 may be made and assembled as follows. Bag 14 and sleeve 13 are thermoformed, such as by injection molding, by known techniques. The bag-sleeve subassembly may be made using solvent or adhesive bonding, depending on the material involved. If bag 14 and sleeve 13 are capable of being solvent bonded, bag 14 is dipped in the mutual solvent and inserted into sleeve 13. When the subassembly is put together by adhesive bonding, bag 14 is dipped into an appropriate adhesive and then inserted into sleeve 13. Membrane 12 may be applied to the bag-sleeve subassembly by spray coating from a solvent system of 90% dichloromethane and 10% trichloroethane.

The following example is intended to further illustrate the above described dispenser and its manufacture. This example is not intended to limit the invention in any way.

Dispensers of the structure shown in FIG. 1 were made as follows using CAB-PMMA blends and, for comparison, pure cellulose acetate butyrate as membrane materials.

Cylindrical flexible bags (2.50 cm long, 4.01 mm I.D. and 4.62 mm O.D.) were injection molded at 176° C., $3.5 \times 10^3$ kPa, from an elastomeric styrene-butadiene copolymer (sold under the trade designation, Kraton 2104).

Osmotic sleeves were prepared for each dispenser as follows. The components (64.5 wt% NaCl, 20 wt% poly(ethylene oxide), molecular weight 600,000, 15 wt% poly(ethylene glycol) of molecular weight 20,000 and 0.5 wt% colloidal $SiO_2$ (sold under the trade name Cabosil) were bulk blended in a Hobart mixer for 20 minutes at low speed. The homogenous powder blend was pressed into 0.6 cm tablets capable of being gravity fed into Arborg injection molding equipment. The osmotic sleeves (2.21 cm long, 4.87 mm I.D., and 5.89 mm O.D.) were formed from the tablets by injection molding at 149° C., $6.5 \times 10^3$ kPa.

Cylindrical plugs of the above described styrene-butadiene copolymer were injection molded. The plugs were 0.5 cm long, had a 4.1 mm O.D., their lower surfaces were recessed hemispherically to a depth of 1.37 mm, and had a central axial bore 0.76 mm in diameter through the length of the plug.

The cylindrical flexible bags were dipped into a 15 wt% cyclohexane solution of the styrene-butadiene copolymer mentioned above and were inserted into the osmotic sleeve. The arcuate surfaces of the plugs were coated with a glue bead of 15 wt% cyclohexane solution of the copolymer and a plug was inserted into the open end of each of the bags. A 22 gauge needle was inserted through the bore of each plug and the plugged bags were placed in an oven at 40° C. for 2 hours.

An outer semipermeable membrane was applied to each bag-sleeve subassembly by coating with a Wurster coater. Three different membrane compositions were used: (1) pure CAB (sold by Eastman Kodak under the designation CAB 500-1), (2) a blend of 75% by weight of the above described CAB and 25% by weight PMMA (sold by Rohm & Haas under the designation VB11-Medical Grade, clear), and (3) a blend of 60% by weight of the above described CAB and 40% by weight of the above-described PMMA. The pure CAB was applied from a 4% solution in methylene chloride and the blends were applied from a 4% solution in a 90:10 mixture of dichloromethane and 1,1,1-trichloroethane. The thickness of the membranes was 0.5 mm. The dispensers were oven-dried at 55° C. for about 5–10 days.

Flow moderators were prepared for each dispenser as follows. Twenty-one gauge needle stock was cut into 2.36 cm lengths. Each length of tubing was circumferentially grooved with 15 grooves, equally spaced 0.3 mm apart along one end of the tube, such that a 4.3 mm distance beginning at one end of the tube is grooved. Caps were insert molded around the grooved portion of the tube 3 mm from the grooved end, from styrene-acrylonitrile copolymer. The caps were hemispherical, 5.6 mm in diameter, with a 0.8 mm diameter diametrical bore. Hemispherical overcaps had a 6.5 mm O.D., were 4.3 mm in length with the bottom hemispherically recessed to a depth of 1.3 mm, had a 0.8 mm diameter diametrical bore through the length of the overcap, and were injection molded from ethylenevinylacetate copolymer. The overcaps were pressed onto the 3 mm grooved extension of the tube.

Figure 2:
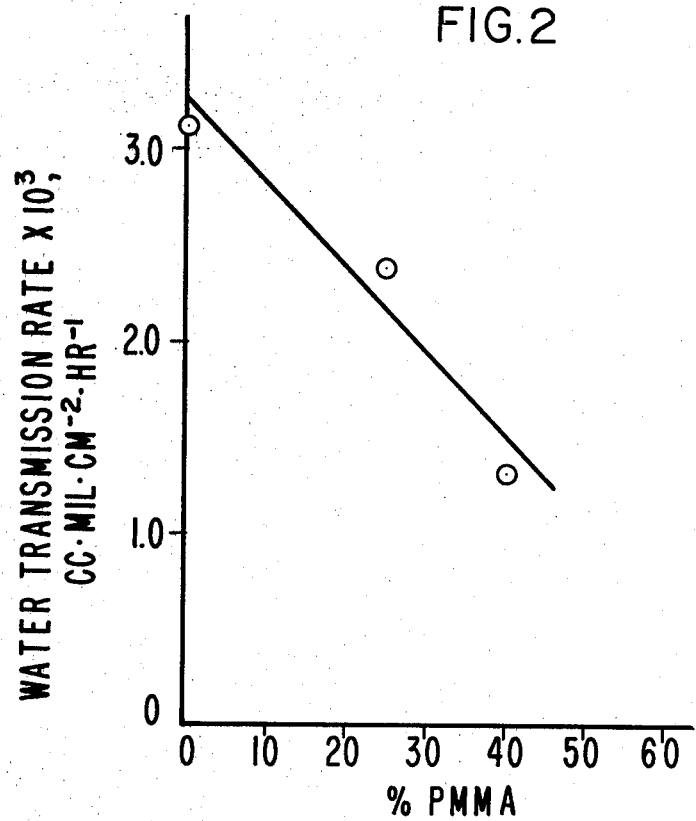
FIG. 2 is a plot of water vapor transmission versus polymethylmethacrylate content of the membranes of the dispensers to the example, infra.

The water transmission rates of the membranes of the dispensers were determined by in vitro pumping rate analysis. These determinations are reported in FIG. 2. As shown, the rates through the CAB-PMMA membranes were significantly lower than the rate through the pure CAB.

The dispensers with the CAB-PMMA blend membranes were filled with a dye solution of FD&C Blue No. 1 in isotonic saline (1w/v%) and placed in isotonic saline at 37° C. The dye solution was pumped from the dispensers at a substantially constant rate of about 0.5 mcl/hr over a two week period.

Modifications of the above described dispensers that are obvious to those of skill in art are intended to be within the scope of the following claims.

We claim:

1. In a fluid dispenser comprising an outer rigid semipermeable membrane that acts as a housing, an inner collapsible bag housed within the membrane that is adapted to contain the fluid, a water-imbibing composition interposed between the outer membrane and the inner bag, and a port that extends from the interior of the bag to the exterior of the dispenser through which the fluid may be charged into the bag and discharged from the bag, the improvement wherein the outer membrane is made from a blend consisting essentially of a major proportion by weight of cellulose acetate butyrate and a minor proportion by weight polymethylmethacrylate.

2. The improvement of claim 1 wherein the cellulose acetate butyrate constitutes about 60% to 90% by weight of the blend and the polymethylmethacrylate constitutes about 10% to 40% by weight of the blend.

* * * * *